United States Patent
Monagle et al.

[11] Patent Number: 5,665,604
[45] Date of Patent: Sep. 9, 1997

[54] METHOD AND APPARATUS FOR DETECTING HALOGENATED HYDROCARBONS

[75] Inventors: Matthew Monagle; John J. Coogan, both of Los Alamos, N. Mex.

[73] Assignee: The Regents of the University of California, Office of Technology Transfer, Alameda, Calif.

[21] Appl. No.: 516,838

[22] Filed: Aug. 18, 1995

[51] Int. Cl.⁶ .................................................. G01N 21/73
[52] U.S. Cl. ............................ 436/139; 422/54; 422/83; 422/90; 436/124; 436/133; 436/141; 436/143; 436/153; 436/154; 436/100; 436/101
[58] Field of Search ............................ 422/54, 83, 90; 436/124, 183, 139, 141, 143, 153, 154, 100, 101

[56] References Cited

U.S. PATENT DOCUMENTS

| | | | |
|---|---|---|---|
| 3,790,348 | 2/1974 | Bossart et al. | 23/254 |
| 4,009,998 | 3/1977 | Benningfield, Jr. | 23/230 |
| 4,032,296 | 6/1977 | Hall | 23/253 |
| 4,224,283 | 9/1980 | Potts | 422/111 |
| 4,547,293 | 10/1985 | King et al. | 210/638 |
| 4,725,412 | 2/1988 | Ito | 422/186.19 |
| 4,778,764 | 10/1988 | Fine | 436/116 |
| 4,804,519 | 2/1989 | Sainz et al. | 422/81 |
| 4,828,800 | 5/1989 | Castleman | 422/83 |
| 4,922,099 | 5/1990 | Masuda et al. | 250/324 |
| 5,015,349 | 5/1991 | Suib et al. | 204/168 |
| 5,055,260 | 10/1991 | Roberge et al. | 422/62 |
| 5,055,266 | 10/1991 | Stetter et al. | 422/83 |
| 5,062,708 | 11/1991 | Liang | 356/316 |
| 5,075,550 | 12/1991 | Miller et al. | 250/338.5 |
| 5,153,139 | 10/1992 | Volz-Thomas et al. | 436/32 |
| 5,272,414 | 12/1993 | Iwanaga | 313/631 |
| 5,316,648 | 5/1994 | Këhn et al. | 204/415 |
| 5,387,775 | 2/1995 | Kang | 219/121.52 |
| 5,427,747 | 6/1995 | Kong et al. | 422/186 |
| 5,458,856 | 10/1995 | Marie et al. | 422/186 |
| 5,468,356 | 11/1995 | Uhm | 204/164 |
| 5,479,254 | 12/1995 | Waskov et al. | 356/316 |

OTHER PUBLICATIONS

Krause et al. "Chemical Dextoxification of Trichloroethylene and 1,1,1-Trichloroethane in a Microwave Discharge Plasma Reactor at Atmospheric Pressure". ACS Symp. Ser. (1993), 518 (Emerging Technologies in Hazardous Waste Management III), 393-410.

G. A. Eiceman et al., "Negative Ion Mobility Spectrometry For Selected Inorganic Pollutant And Gas Mixtures In Air," 58 Anal. Chem. No. 1, pp. 76-80 (1986).

Primary Examiner—Jill Warden
Assistant Examiner—Sharidan Carrillo
Attorney, Agent, or Firm—Ray G. Wilson

[57] ABSTRACT

A halogenated hydrocarbon (HHC) detector is formed from a silent discharge (also called a dielectric barrier discharge) plasma generator. A silent discharge plasma device receives a gas sample that may contain one or more HHCs and produces free radicals and excited electrons for oxidizing the HHCs in the gas sample to produce water, carbon dioxide, and an acid including halogens in the HHCs. A detector is used to sensitively detect the presence of the acid. A conductivity cell detector combines the oxidation products with a solvent where dissociation of the acid increases the conductivity of the solvent. The conductivity cell output signal is then functionally related to the presence of HHCs in the gas sample. Other detectors include electrochemical cells, infrared spectrometers, and negative ion mobility spectrometers.

12 Claims, 4 Drawing Sheets

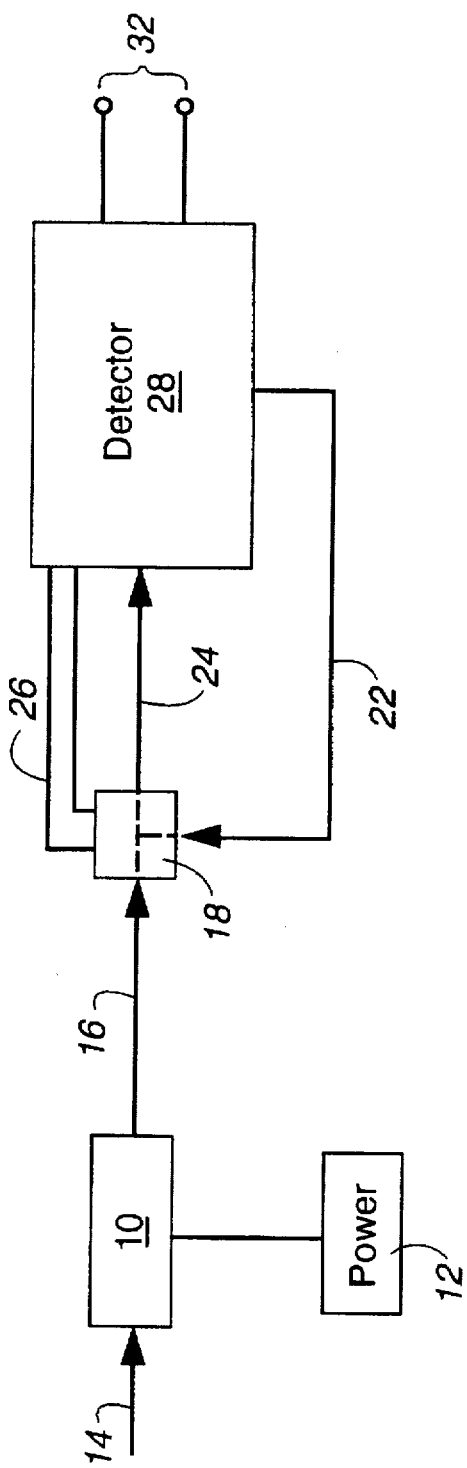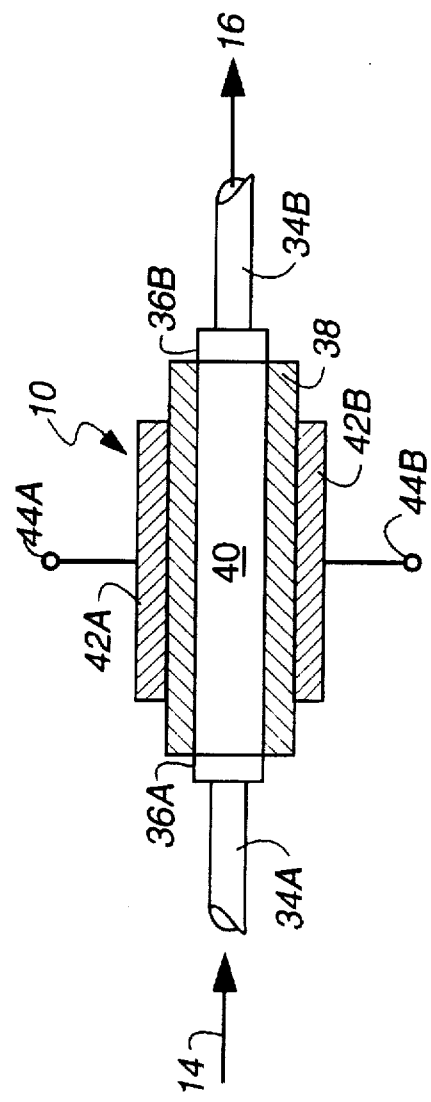

1

METHOD AND APPARATUS FOR DETECTING HALOGENATED HYDROCARBONS

BACKGROUND OF THE INVENTION

This invention relates to the detection of halogenated hydrocarbons, and, more particularly, the application of a silent discharge plasma to form detectable components from the hydrocarbons. This invention was made with government support under Contract No. W-7405-ENG-36 awarded by the U.S. Department of Energy. The government has certain rights in the invention.

Volatile organic compounds (VOCs) are rather widespread contaminants and there are many sites that must be examined to determine the presence/absence of such contaminants. The presence of VOCs, such as halogenated hydrocarbons (HHCs), may require expensive remediation of the site, although small quantities may be in compliance with the Clean Air Act and other environmental requirements. In view of the liabilities now associated with the acquisition of contaminated sites, there is a need for a rapid and inexpensive field screening technology that could accurately determine the presence/absence of HHCs.

Even the capability to quickly and inexpensively eliminate sites from further consideration as contaminated sites is of substantial value. It is estimated that the cost of fixed base analysis is on the order of $350/sample and adequate site sampling might involve hundreds or thousands of samples. An initial field screening could eliminate the need for laboratory testing at many locations within a site so that only areas with actual contamination might require fixed base analyses.

Accordingly, it is an object of the present invention to provide an HHC detector that can be used in the field and that has a sensitivity effective to determine the presence of HHCs at levels below statutory limits.

It is another object of the present invention to provide an inexpensive and portable HHC detector.

One other object of the present invention is to provide an HHC detector that minimizes the generation of toxic waste products.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a halogenated hydrocarbon (HHC) detector. A silent discharge plasma device receives a gas sample that may contain one or more HHCs and produces excited electrons and free radicals for oxidizing the HHCs in the gas sample to produce water, carbon dioxide, and an acid including halogens in the HHCs. A conductivity cell combines the oxidation products with a solvent where dissociation of the acid increases the conductivity of the solvent. The conductivity cell output signal is then functionally related to the presence of HHCs in the gas sample.

In another characterization of the invention a process provides for the sensitive detection of HHCs in a gas sample. A gas sample that may contain one or more HHCs is directed through a silent discharge device that generates excited electrons and free radicals for oxidizing the HHCs to produce water, carbon dioxide, and acids containing the HHC halogens. The oxidation products are combined with a solvent in a conductivity cell where dissociation of the acids increases the conductivity of the solvent. The output signal from the conductivity cell is functionally related to the presence of HHCs in the air sample.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1 is a schematic diagram of a halogenated hydrocarbon detector system according to one embodiment of the present invention.

FIG. 2 is a cross-sectional representation of a silent discharge plasma cell for use in the system shown in FIG. 1.

DETAILED DESCRIPTION OF THE INVENTION

Figure 3A:
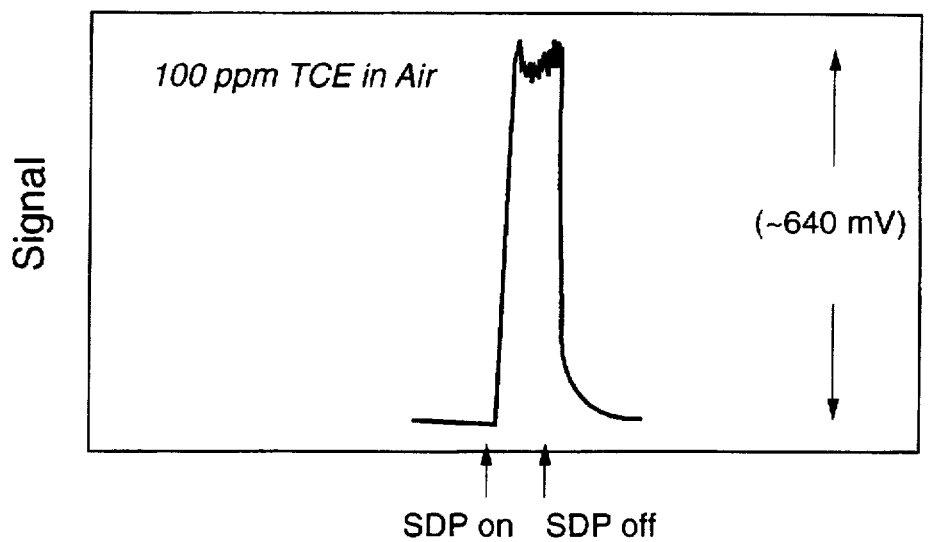
FIGS. 3A, 3B, and 3C are exemplary conductivity cell outputs from the system shown in FIG. 1.

In accordance with the present invention, a silent discharge plasma (SDP) device (also known as a dielectric barrier discharge device) generates free radicals and excited electrons from gas flowing through the device, where the gas may contain halogenated hydrocarbons (HHCs) from a suspect site. The gas may be air collected from the site that is to be monitored. Free radicals produced by the SDP oxidize the HHCs to produce $H_2O$, $CO_2$, and HX, where X is a halogen, which is typically fluorine (F), chlorine (Cl), or bromine (Br). Silent discharge plasmas provide an alternative to thermal oxidation, where electrical discharges produce free radicals in concentrations effective to completely oxidize small quantities of HHCs, such as trichloroethylene (TCE), carbon tetrachloride, perchloroethylene, and the like. A detector capable of detecting HX then outputs a signal that is indicative of the presence of HHCs in the sample.

An SDP cell efficiently produces free radicals of O(3P) and OH that provide oxidation rates associated with electron temperatures of 10,000 to 100,000 K, while the reactions occur near ambient temperatures. These "cold plasmas" operate at atmospheric pressure and the energy in the plasma drives the chemical reactions rather than generating heat energy. Using a dielectric and an alternating high voltage (50 or 60 Hz to several kHz power frequency), the SDP cell creates substantial quantities of the plasma in the form of "micro-discharges" in the gas. These microdischarges are statistically spread in space and time, filling the entire sample volume with concomitant high destruction efficiencies for organic compounds.

Detection of the halogenated hydrocarbons is obtained with a variety of detectors, e.g., conductivity cell, electrochemical cell, ion mobility spectrometry (IMS), and infrared spectrometry. In one exemplary embodiment, the oxidized sample is moved out of the SDP reactor region and into a conductivity cell where the acid dissociates in a solvent. The dissociated acid increases the conductivity of the solvent. The change in the conductivity of the solvent is detected and a signal is produced. The solvent is continuously circulated from a reservoir, where the acid is removed by ion-exchange equipment before the solvent is returned to the reservoir.

FIG. 1 depicts a block diagram of a halogenated hydrocarbon monitor according to one embodiment of the present invention using a conductivity cell. SDP cell 10, discussed below, is powered with a high voltage ac power supply 12, typically 5–15 kV at 60 Hz to 60 kHz. Sample air source is input to cell 14. The sample may be injected via a syringe or a gas sampling bottle, or a Tedlar™ bag. The sample is then moved into cell 10 using high purity air supplied from an air compressor or sample air bottle (not shown) which has been filtered (not shown) with a charcoal filter before input to cell 10. In an alternate embodiment, ambient air is drawn through cell 10. No gas bottles or filters are used. SDP cell 10 oxidizes the HHC sample to $H_2O$, $CO_2$, and HX, where X is the halogen (Cl, F, Br) within the HHC. It will be understood that the operating parameters of SDP cell 10 are optimized as a function of the HHCs expected to be present in the sample gas. For example, for a 50 sccm flow through the cell, a few watts of power are applied to the cell in order to assure destruction of all of the possible HHCs to their corresponding acids. SDP cell operating parameters include gas pressure, gas flow rate, applied power, cell temperature, relative humidity, dielectric barrier thickness, and discharge area.

Effluent gas 16 from SDP cell 10 is transported to detector 18, which may be a conductivity cell in this embodiment, and mixed with a suitable solvent, e.g., 1-propanol. The HX dissolves and dissociates in the solvent, creating ionic species that are then detected by conductivity cell 18. Signal 26 is output from conductivity cell 18 to signal detector 28. Signal detector 28 may provide some indication of solvent conductivity or output a signal 32 to a recording device, such as a strip recorder (not shown) to provide a record of the sample analyses. Signal detector 28 also circulates the solvent through input line 22 and output line 24 and removes the dissolved species from the solvent, e.g., by flowing the solvent through ion exchange cartridges 25.

The sensitivity of conductivity cell 18 is optimized with respect to the particular HHC and solvent to be input through the cell. For example, fluorobenzene does not provide a particularly sensitive sample since each molecule of analyte has only one available fluorine to create HF. Conductivity cell parameters include solvent pump speed, gas flow into the cell, analyte solubility in solvent (e.g., HF>HCl>HBr), and cleanliness of ion exchange cartridges in detector 28.

An exemplary SDP cell 10 is shown in a cross-sectional view in FIG. 2. Dielectric glass plate 38 forms sample volume 40. Sample gas 14 is flowed though inlet tube 34A, connected to volume 40 through fitting 36A, into volume 40 and effluent gas 16 is output through fitting 36B and outlet tube 34B. The edge between electrodes 42A and 42B and glass plate 38 is sealed by, e.g., epoxy or RTV. The planar geometry shown in FIG. 2 is exemplary only and alternate geometries, e.g., a cylindrical geometry might be used. Electrodes 42A and 42B are connected to power supply 12 (FIG. 1) through electrical leads 44A and 44B, respectively.

When sufficient voltage is applied across the gas gap so that the ionization rate exceeds the electron attachment rate, a streamer forms, transporting charge across the gap, and depositing charge on the surface of the dielectric. This surface charge opposes the driving field, and when enough surface charge accumulates to reduce the field to the point where attachment again dominates, the streamer is extinguished. The individual streamers, called microdischarges, have a lifetime, dependent upon pressure and gas, of only a few nanoseconds. The presence of the dielectric, such as glass, allows the generation of nanosecond discharges from the application of line frequency (60 Hz) voltage. The use of higher frequencies allow for greater power densities, but do not affect the nature of the microdischarge. Because of the transient nature of the discharge, only the lightest particles, the electrons, can extract any energy from the field. Thus, while the gas remains at ambient temperatures, the electrons are easily excited up to 10 eV, an effective temperature greater than 100,000 K and an ideal energy range to break chemical bonds and excite atomic and molecular species. Other plasma sources, inductively coupled plasmas, RF plasmas, and flow discharges, are unable to generate such energetic electrons. Silent discharges combine the advantages of volumetric, transient, and atmospheric plasma source.

Figure 3B:
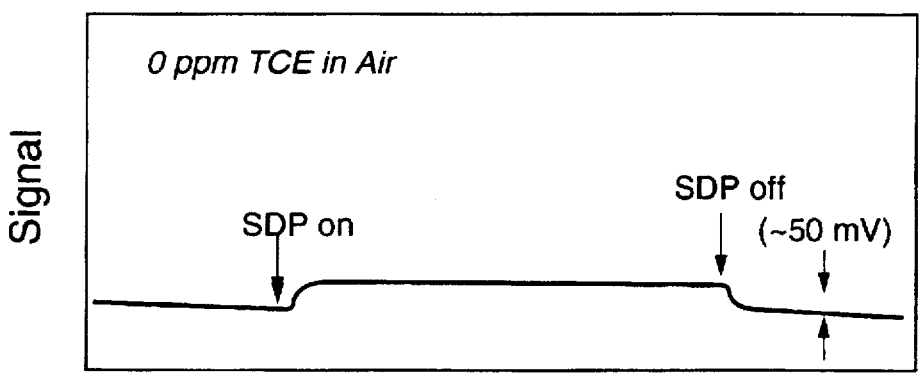
Figure 3C:
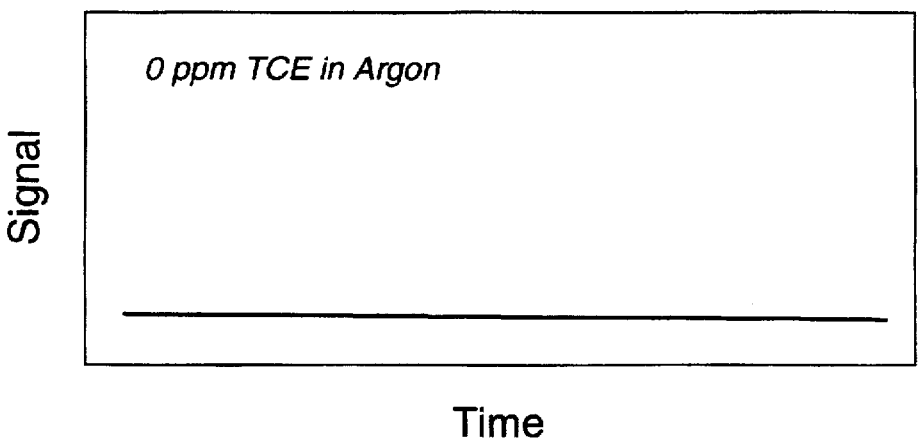

Exemplary system outputs from a conductivity cell-based system are shown in FIGS. 3A, 3B, and 3C for trichloroethylene (TCE) and a 1-propanol solvent. FIG. 3A illustrates a detected output from a sample having a concentration of 100 ppm TCE in air. An output signal is immediately apparent when the SDP cell is turned on; the signal decays rapidly when the SDP cell is turned off and the sample air is swept from the SDP cell. FIG. 3B shows that an air sample carrier with 0 ppm HHC provides a slight output signal when the SDP cell is turned on, but this carrier signal can be readily distinguished from the signal with TCE present. When an inert gas, such as argon, is used as the carrier, as shown in FIG. 3C, the conductivity detector output signal is effectively zero.

In one alternate embodiment, detector 18 (FIG. 1) is an electrochemical cell for the detection of the analytical species that result from the oxidation process. A suitable cell is an electrochemical wet cell with a gas permeable membrane (available from Exidyne) to detect HX, such as HCl. The electrochemical cell is applicable to a variety of compounds that can be oxidized to create species that can be detected electrochemically.

Figure 4A:
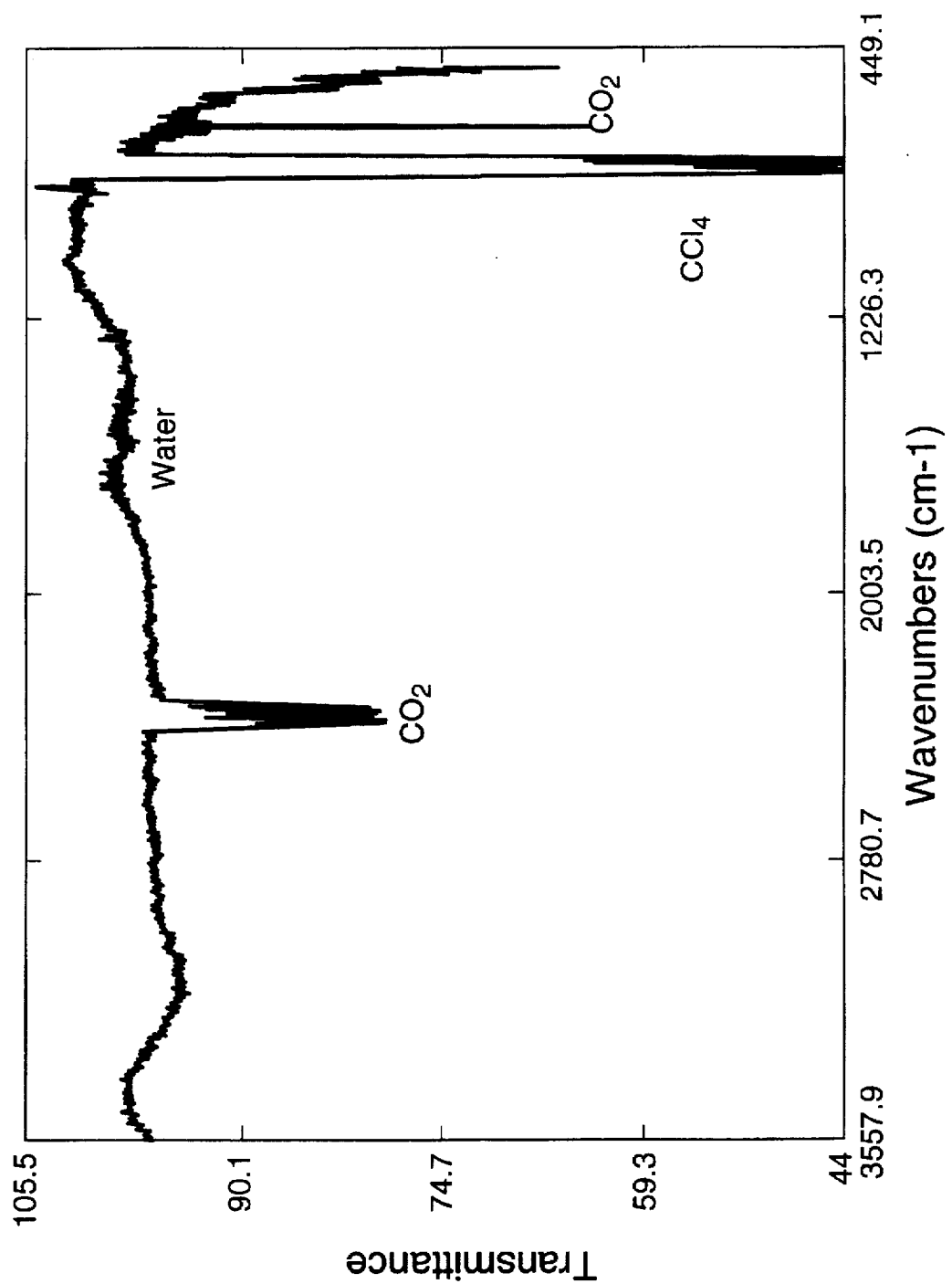
FIGS. 4A and 4B are exemplary outputs from an embodiment of the invention using an infra-red spectrometer.
Figure 4B:
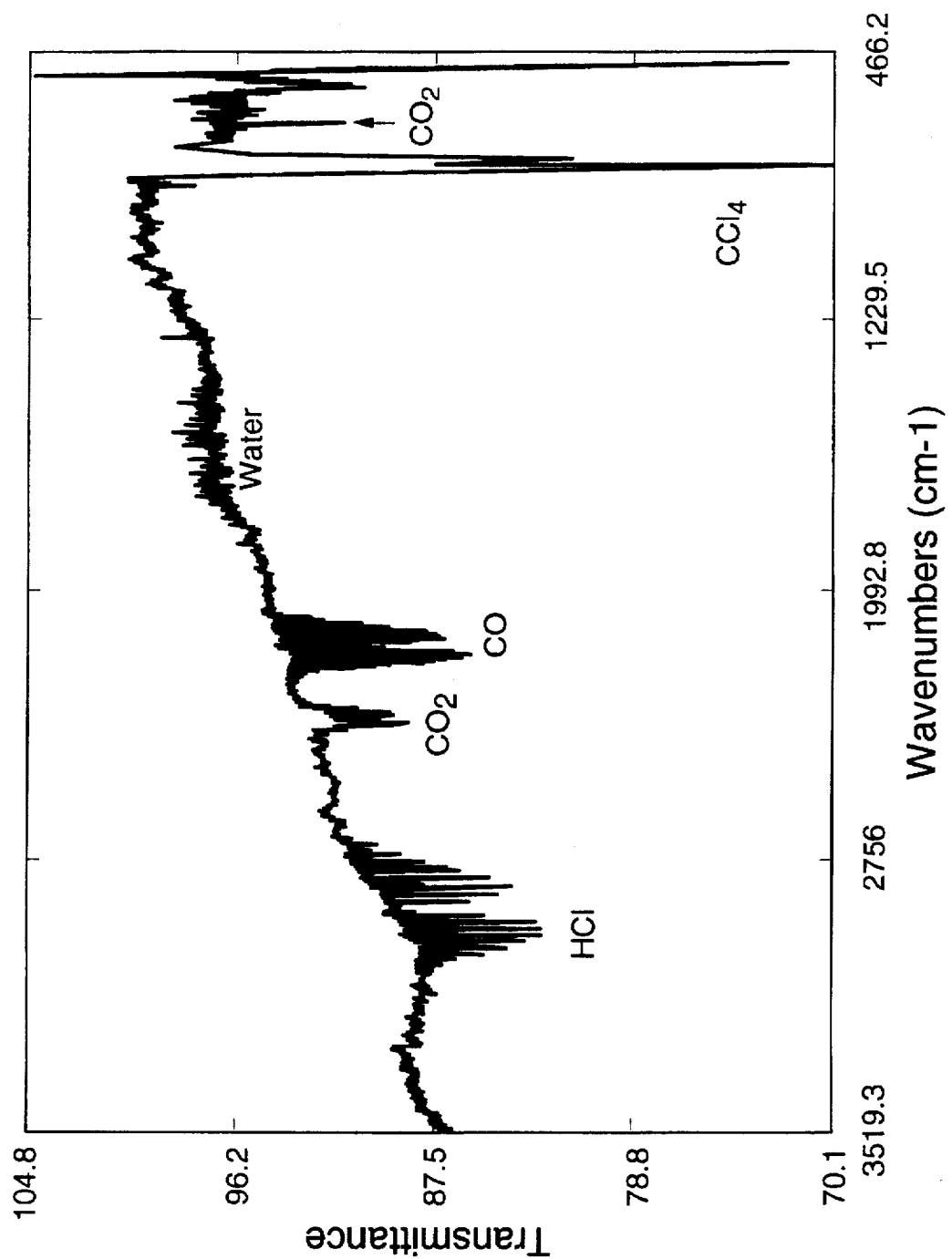

In one other alternate embodiment, detector 18 (FIG. 1) is a Fourier-transform infra-red (IR) spectrometer. FIG. 4A is an output spectrum of an HHC sample in air, here carbon tetrachloride, before SDP cell 10 (FIG. 1) is turned on. When SDP cell 10 is turned on, a spectrum component (here HCl) that is characteristic of the HHC is readily apparent, as shown in FIG. 4B.

In yet another embodiment, detector 18 (FIG. 1) is a negative ion mobility spectrometer, as described in G. A. Eiceman, et al., "Negative Ion Mobility Spectrometry for Selected Inorganic Pollutant Gases and Gas Mixtures in Air," 58 Anal. Chem., pp. 76–80 (1986), incorporated herein by reference. Negative ion mobility spectrometry can distinguish acids, such as HCl, at concentrations at least as low as 1 ppb.

The system shown in FIG. 1 using a conductivity cell has been applied to several HHCs, including freons, trichloroethane (TCA), trichloroethylene (TCE), carbon tetrachloride, bromoform and fluorobenzene. These compounds are representative of the capability of the detector to measure a wide range of HHCs, including brominated and fluorinated organics. The following compounds have been evaluated using a detector with a conductivity cell:

| | |
|---|---|
| 112 TCA | down to 50 ng/mL with 5 mL injected (0.25 µg) |
| 111 TCA | down to 202 ng/mL with 1 mL injected (0.25 µg) |
| Fluorobenzene | down to 15 mg/mL with 0.5 mL injected (7.5 µg) |
| Bromoform | down to 8.77 mg/mL with 0.5 mL injected (4.35 µg) |
| Carbon tetrachloride | down to 24 mg/mL with 0.5 mL injected (12 µg) |
| Freon 11 | down to 32 mg/mL with 0.2 mL injected (0.45 µg |

The system shown in figure has also been evaluated using an HCI selective electrochemical cell. The following compounds were evaluated:

| | |
|---|---|
| Methylene chloride | down to 35 ng/mL with 2 mL injected (70 µg) |
| Chlorobenzene | down to 33 ng/mL with 2 mL injected (66 µg) |
| Fluorobenzene | no appreciable response (none expected) |
| Bromobenzene | down to 32 mg/mL with 0.5 mL injected (70 µg) |
| Carbon tetrachloride | down to 35 mg/mL with 2 mL injected (64 µg) |
| Freon 113 | down to 32 mg/mL with 2 mL injected (64 µg |

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A sensitive halogenated hydrocarbon (HHC) detector comprising:
   a silent discharge plasma device connected to receive an air sample that may contain one or more HHCs and to produce free radicals that oxidize said HHCs to produce water, carbon dioxide, and one or more acids including halogens forming said HHCs; and
   to said silent discharge plasma device a detector connected to receive said water, carbon dioxide, and one or more acids, and effective to detect said one or more acids and to output an electrical signal indicative of the presence of said one or more HHCs.

2. An HHC detector according to claim 1, wherein said detector is a conductivity cell effective to dissolve said one or more acids in a solvent, whereby said one or more acids dissociate to increase electrical conductivity of said solvent.

3. An HHC detector according to claim 2, further including a solvent circulation system with an ion exchanger for removing dissociated ion species from said solvent.

4. An HHC detector according to claim 1, wherein said detector is an electrochemical cell.

5. An HHC detector according to claim 1, wherein said detector is an infra-red spectrometer.

6. An HHC detector according to claim 1, wherein said detector is a negative ion mobility spectrometer.

7. A process for the sensitive detection of halogenated hydrocarbons (HHCs) in an air sample that may contain one or more of said HHCs comprising the steps of:
   directing said air sample through a silent discharge device that generates free radicals;
   oxidizing said one or more HHCs with said free radicals to produce water, carbon dioxide, and an acid containing one or more halogens from said HHCs;
   detecting the presence of said acid; correlating a presence of halogenated hydrocarbons (HHCs) to said presence of said acid; and
   outputting a signal indicative of the presence of said HHCs in said gas sample.

8. A method according to claim 7, wherein the step of detecting the presence of said acid further comprises the steps of:
   dissolving said one or more acids in a solvent; and
   detecting an electrical conductivity of said solvent to determine the presence of said one or more acids in said solvent.

9. A process according to claim 8, further including the step of circulating said solvent through an ion exchanger to remove ion species dissolved in said solvent.

10. A process according to claim 7, including the step of: inputting said acid to an electrochemical cell.

11. A process according to claim 7, including the step of: inputting said acid to an infra-red spectrometer.

12. A process according to claim 7, including the step of inputting said acid to a negative ion mobility spectrometer.

* * * * *